US006620422B1

United States Patent
Maquin et al.

(10) Patent No.: US 6,620,422 B1
(45) Date of Patent: Sep. 16, 2003

(54) COMPOSITIONS CONTAINING A PEPTIDE AND POLYLACTIC-GLYCOLIC ACID SUITABLE FOR PREPARING SUBCUTANEOUS IMPLANTS WITH AN EXTENDED RELEASE PERIOD

(75) Inventors: Alain Maquin, Lagny sur Marne (FR); Patrice Mauriac, Paris (FR); Pierre Marion, Neuilly Plaisance (FR)

(73) Assignee: Mediolanum Farmaceutici S.p.A., Milan (IT)

( * ) Notice: Subject to any disclaimer, the term of this patent is extended or adjusted under 35 U.S.C. 154(b) by 0 days.

(21) Appl. No.: 09/857,404

(22) PCT Filed: Dec. 6, 1999

(86) PCT No.: PCT/EP99/09536

§ 371 (c)(1),
(2), (4) Date: Jun. 1, 2001

(87) PCT Pub. No.: WO00/33809

PCT Pub. Date: Jun. 15, 2000

(30) Foreign Application Priority Data

Dec. 10, 1998 (IT) .......................................... MI98A2655

(51) Int. Cl.[7] .............................. A61K 9/00; A61K 9/16; A61K 38/00; A61K 38/24; A61K 47/30
(52) U.S. Cl. ....................... 424/422; 424/425; 424/484; 424/486; 514/2; 514/12; 514/14; 514/15
(58) Field of Search ............................. 424/484, 486, 424/487, 489, 497, 422, 423, 426; 514/2, 12, 14, 15

(56) References Cited

U.S. PATENT DOCUMENTS

| 5,134,122 A | * | 7/1992 | Orsolini | 514/15 |
| 5,192,741 A | * | 3/1993 | Orsolini | 514/4 |
| 5,445,832 A | * | 8/1995 | Orsolini | 424/491 |

FOREIGN PATENT DOCUMENTS

| WO | WO 92/11843 | * | 7/1992 | |
| WO | WO9211843 | | 7/1992 | ............ A61K/9/20 |
| WO | WO9809613 | | 3/1998 | ............ A61K/9/00 |
| WO | WO 98/09613 | * | 3/1998 | |

OTHER PUBLICATIONS

Hsu et al., "In Vitro Controlled Release of Isoniazid From Poly(lactide–co–glycolide) Matrices", *Journal of Controlled Release* Oct. 31 No. 3, (1994).

* cited by examiner

Primary Examiner—Thurman K. Page
Assistant Examiner—Rachel M. Bennett
(74) Attorney, Agent, or Firm—Abelman, Frayne & Schwab

(57) ABSTRACT

Compositions comprising a peptide and polylactic-glycolic acid (PLGA) wherein the distribution of the size of the particles of the peptide in the PLGA results highly heterogeneous, suitable to the preparation of subcutaneous implants having a release time at least equal to 6 months.

22 Claims, 8 Drawing Sheets

US 6,620,422 B1

COMPOSITIONS CONTAINING A PEPTIDE AND POLYLACTIC-GLYCOLIC ACID SUITABLE FOR PREPARING SUBCUTANEOUS IMPLANTS WITH AN EXTENDED RELEASE PERIOD

This application is a 371 of PCT/EP 99/09536 P/ED Jun. 12, 1999.

1. Field of the Invention

The present invention refers to compositions comprising a peptide and polylactic-glycolic acid suitable for the preparation of subcutaneous implants.

2. Prior Art

Compositions made up of mixtures of a drug with a polymer of lactic acid or a polymer of glycolic acid or with a copolymer of lactic acid and glycolic acid, as described in the U.S. Pat. No. 3,773,919 (Du Pont) are well known.

These compositions are indicated for parenteral administration and have the characteristics of releasing effective quantities of the drug over a set period of time.

The drug and the polymeric substance can be combined in accordance with any of the known techniques or the particles of the drug can be coated in the polymer operating in accordance with known techniques.

The U.S. Pat. No. 4,767,628 (ICI) describes compositions containing a peptide and a polymer of lactic acid or a copolymer of lactic acid and glycolic acid.

When preparing the compositions, the peptide and the (co)polymer are dissolved in a solvent which can be the same or different for the two substances, for Example dioxane or water, and then the two solutions are mixed.

The subsequent operations consist of removing the solvent at low temperature and in extruding the powder obtained in this way.

In this way a composition in the form of cylinders is obtained in which the peptide is distributed homogeneously throughout the polymer.

It is already known from the U.S. Pat. No. 5,366,734 (Zeneca) that the compositions covered by the U.S. Pat. No. 4,767,628 referred to above can be used in preparing subcutaneous implants.

The polymer of lactic acid and the copolymer of lactic acid and glycolic acid are incompatible with the peptide therefore diffusion of the peptide through the polymer is impossible.

When these implants are introduced into a buffer solution at 37° C., the water penetrates and diffuses in the implant and is distributed between the polymer and the peptide forming regions of hydrated peptides.

The first stage in releasing the peptide described in the U.S. Pat. No. 5,366,734 is a stage of diffusion caused by the polymer swelling.

When the polymer swells this allows channels of hydrated peptide to form where the peptide diffuses to the surface.

If swelling stops, the peptide is no longer released.

The second stage of release is caused by the polymer matrix degrading.

During this stage holes and cracks form in the matrix which allow the release of the hydrated peptides which are still isolated in the matrix.

The total release time is limited to the sum of the release times for each stage. However the maximum release time observed is in the order of three months.

In the application for international patent WO 98/09613 (Deghenghi) a process for preparing subcutaneous implants capable of releasing bioactive peptides is described.

This process consists of the following stages:

milling a copolymer of lactic acid and glycolic acid, wetting the copolymer with an aqueous slurry of a peptide (in the Examples an aqueous solution of avoreline acetate is used):

mixing this copolymer with the aforementioned slurry so as to obtain a homogeneous mixture;

drying this mixture at a temperature of no higher than 25° C.;

extruding the mixture at 70–110° C. in order to obtain small extruded cylinders suitable for use as subcutaneous implants.

This process cannot be carried out using industrial methods because it is not possible to sufficiently eliminate water from the mixture. The results declared in WO 98/109613 cannot therefore be reproduced.

However the fundamental characteristic of the compositions for subcutaneous implants in the patents referred to above consists of the homogeneous distribution of the peptide in the polymeric substance, resulting from using a solution of at least one of the two components.

The implants currently on the market have the disadvantage of releasing the peptides over a limited period of time, generally of around 3 months.

SUMMARY OF THE INVENTION

The applicant has now found compositions suitable for preparing subcutaneous implants which allow the active substance to be released over a period of time of at least 6 months.

These compositions consist of a polylactic-glycolic acid (PLGA) and a peptide and have the characteristic of distributing peptide particles in the PLGA whose dimensions, under microscopic examination, are extremely heterogeneous, with peptide particles of diameter of between 1 and 60 micrometres dispersed in the polymer matrix.

These and other characteristics of the compositions in accordance with the invention and the process for preparing them will be illustrated in greater depth in the following detailed description.

DETAILED DESCRIPTION OF THE INVENTION

Figure 1:
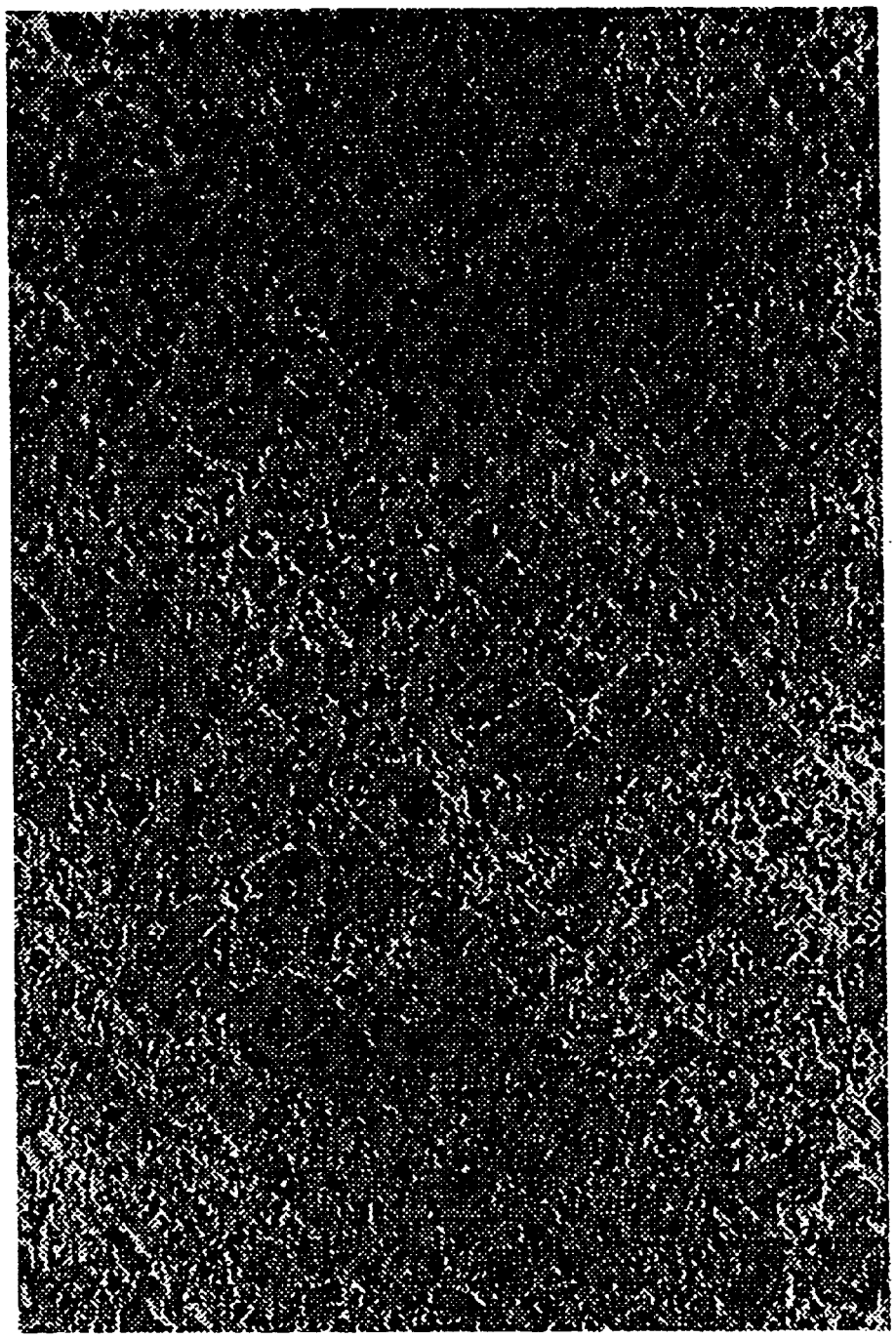
FIG. 1 represents a microscope test of a cross section of an implant according to the invention.

This invention refers to compositions consisting of polylactic-glycolic acid (PLGA) and a peptide suitable for the preparation of long-release subcutaneous implants.

The implants prepared from compositions in accordance with this invention consist of a PLGA matrix of a high molecular weight incorporating a peptide in the form of particles having extremely heterogeneous dimensions.

This structure allows the peptide to be released in three stages, which are, respectively: pure diffusion, diffusion with swelling of the PLGA and release caused by PLGA degradation.

This allows the total release time to be significantly increased.

When these implants are introduced into an aqueous environment the water diffuses through the polymer matrix, reaches the peptide particles closest to the surface and then the more internal zones, resulting in the formation of a porous lattice of the hydrated peptide, through which the phenomenon of peptide release via pure diffusion (first stage) occurs.

The implant remains unchanged for approximately 6 weeks and over this period releases approximately 30% of the peptide.

The duration of this pure diffusion stage is essentially determined by the degree of heterogeneity of the dimensions of the peptide particles and the speed is essentially determined by the peptide content in the PLGA matrix.

As a result of the wide diversity in the dimensions of the peptide granules, a sufficient quantity of peptide remains after the first stage of dissolution to be released over the subsequent stages.

In the second stage the peptide is released by diffusion with swelling of the polymer.

In the third stage, the residual peptide is released when the matrix is destroyed.

The succession of the three stages for releasing the peptide without dead time depends on the appropriate choice of constituents in the composition, in particular:

the heterogeneous nature of the dimensions of the peptide particles determines the first stage of release;

the characteristics of the PLGA (molecular weight and molar ratio) have an influence on the stages of the swelling and matrix degradation.

The technical difficulty of this invention lies in retaining the heterogeneous nature of the dimensions of the peptide particles throughout the process for preparing the implants.

This difficulty cannot be overcome by using the known techniques of mixing by dissolving in a solvent shared by the two compounds or in one solvent for one of the two compounds, nor by means of the techniques for mixing in the melted state.

This difficulty has been resolved in this invention by means of wet granulation of the PLGA with the peptide. This operation and the subsequent operations allow the initial heterogeneity of the peptide particles to be retained.

The invention also refers to the process for preparing these compositions and to the aforementioned subcutaneous implants.

One such process is a wet granulation process.

This process consists of the following stages:

a) the peptide in the form of particles having a diameter of between 1 and 60 micrometres is homogeneously mixed when dry with PLGA in the form of particles whose granulometry is between 10 to 150, preferably 50 and 150, micrometres;

b) the mixture obtained from stage a) is granulated using wet granulation by adding a suitable liquid, for example ethanol or water;

c) the granulate is then dried until the residual liquid content is 0.1–3.0%, preferably 0.5–2.0% by weight. This liquid content is fundamental in that it gives the granule sufficient cohesion to prevent the constituents of the mixture from separating during subsequent treatments;

d) the mixture obtained from stage c) is extruded. Exposure time in the extruder is from between 1 and 10, preferably between 4 and 6 minutes, with a temperature profile which ranges from 20° C., preferably 30° C., on entering the extruder to no higher than 120° C., preferably 110° C., on leaving the extruder. Under these conditions the PLGA melts forming a continuous matrix which coats the peptide particles while maintaining the heterogeneous nature of these particle dimensions.

e) the cylinders produced from extrusion may be slightly stretched and then cut to obtain dimensions suitable for the subcutaneous implants, namely a diameter of between 1.0 and 1.7, preferably between 1.3 and 1.5 mm, and a length of between 10 and 30, preferably between 15 and 24 mm;

f) finally, if needed, the cylinders obtained from stage e) are sterilised.

Suitable polylactic-glycolic acid copolymers for use in the invention have molecular weights ranging from 50,000 to 150,000 and a molar ratio between the lactic acid and the glycolic monomer comprised between 50:50 and 95:5.

Preferred polylactic-glycolic acid (PLGA) to be used in the process in accordance with this invention has a high nominal molecular weight, of between 100,000 and 150,000 D, and a molar ratio between lactic monomer and glycolic monomer of between 70/30 and 75/25.

The peptides which can be used in this invention are preferably, but not exclusively, analogues of LHRH and comprise, for example avoreline: 5-oxo-L-prolyl-L-histidil-L-tryptophil-L-seryl-L-tyrosil-2-methyl-D-tryptophil-L-leucyl-L-arginyl-N-ethyl-prolylamide; tryptoreline: 5-oxo-L-prolyl-L-histidyl-L-tryptophil-L-seryl-L-tyrosil-D-tryptophil-L-leucyl-L-arginyl-L-prolyl-glicinamide; leuproreline: 5-oxo-L-profil-L-histidyl-L-tryptophil-L-seryl-L-tyrosil-D-1eucyl-L-leucyl-L-arginyl-N-etil-L-prolylamide; gosereline: 5-oxo-L-prolyl-L-histidyl-L-tryptophil-L-seryl-L-tyrosil-tert-butyl-D-seryl-L-leucyl-L-arginyl-L-prolyl-NH—NH—CO—$NH_2$.

The peptide preferable used in this invention is avoreline.

The content of peptide in the composition is between 20 and 40%, preferably between 20 and 36% by weight.

The quantity of liquid added for granulation is between 10 and 60, preferably between 20 and 45 parts by weight in comparison with the mixture.

The desiccation involved in stage c) takes place at a temperature of between 20–50, preferably between 20–30° C. in a current of dry air.

The transversal section of the cylinders obtained from stage f) reveals under microscope a heterogeneous structure containing peptide particles having the same granulometry as the initial peptide immersed in the matrix constituted by the PLGA.

The cylinders obtained from stage f) can be successfully used for subcutaneous implants.

Each implant having a diameter of between 1.0 and 1.7, preferably between 1.3 and 1.5 mm, and a length of between 10 and 30, preferably between 15 and 24 mm, has a peptide content of between 5 and 20 mg.

The peptide released during in vitro and in vivo trials takes place over a time period of at least 6 months.

However the overall time for releasing the peptide can be controlled by varying the diameter and the length of the implant.

Clinical trials conducted using subcutaneous implants in accordance with this invention in patients with prostate tumours have shown the testosterone suppression within 4 weeks with this effect lasting from approximately 7 months to approximately 12 months.

In order to illustrate the invention the following Examples are quoted.

EXAMPLE 1

10 grams of avoreline were mixed thoroughly with 30 grams of polylactic-glycolic acid (PLGA).

The avoreline had the following characteristics:
acid-alkalimetric titer: 88.1 % by weight;
pKa: 6.15–9.70–12.02;
granulometric distribution : between 1 and 60 micrometres.

The PLGA had the following characteristics:
molecular weight of 116,500 D;
molar ratio between lactic monomer and glycol monomer: 70:30;
intrinsic viscosity ($CHCl_3$); 0.98 dl/g measured at 25° C.,
granulometric distribution: in 90% of cases between 50 and 150 micrometres.

The mixture obtained was granulated wet by adding 16 ml of ethanol using a 16 mm grid.

The granulate obtained was desiccated for 12 hours at a temperature of 25° C. in a current of dry air.

After drying the ethanol content in the granulate was 0.66% by weight.

Finally the granulate was extruded using an extruder with a die head of diameter 1.5 mm and length 17.55 mm.

The speed of rotation of the screws was 5 rev/minute and the temperature was 30° C. on entering the extruder and 100° C. on leaving the extruder.

The cylinder obtained by the extrusion was slightly stretched and then cut into segments of length 18 mm which were finally radiosterilised. In this way implants for subcutaneous use with diameter of 1.5 mm, length 18 mm and avoreline content of 25.3% by weight were obtained.

The transversal section of these implants examined under microscope under ×275 enlargment reveals a heterogeneous distribution of the particles of avoreline in the mass of PLGA, as shown in FIG. 1. In particular the particles of avoreline retain their initial granulometry of between 1 micrometre ad 60 micrometre.

Figure 2:
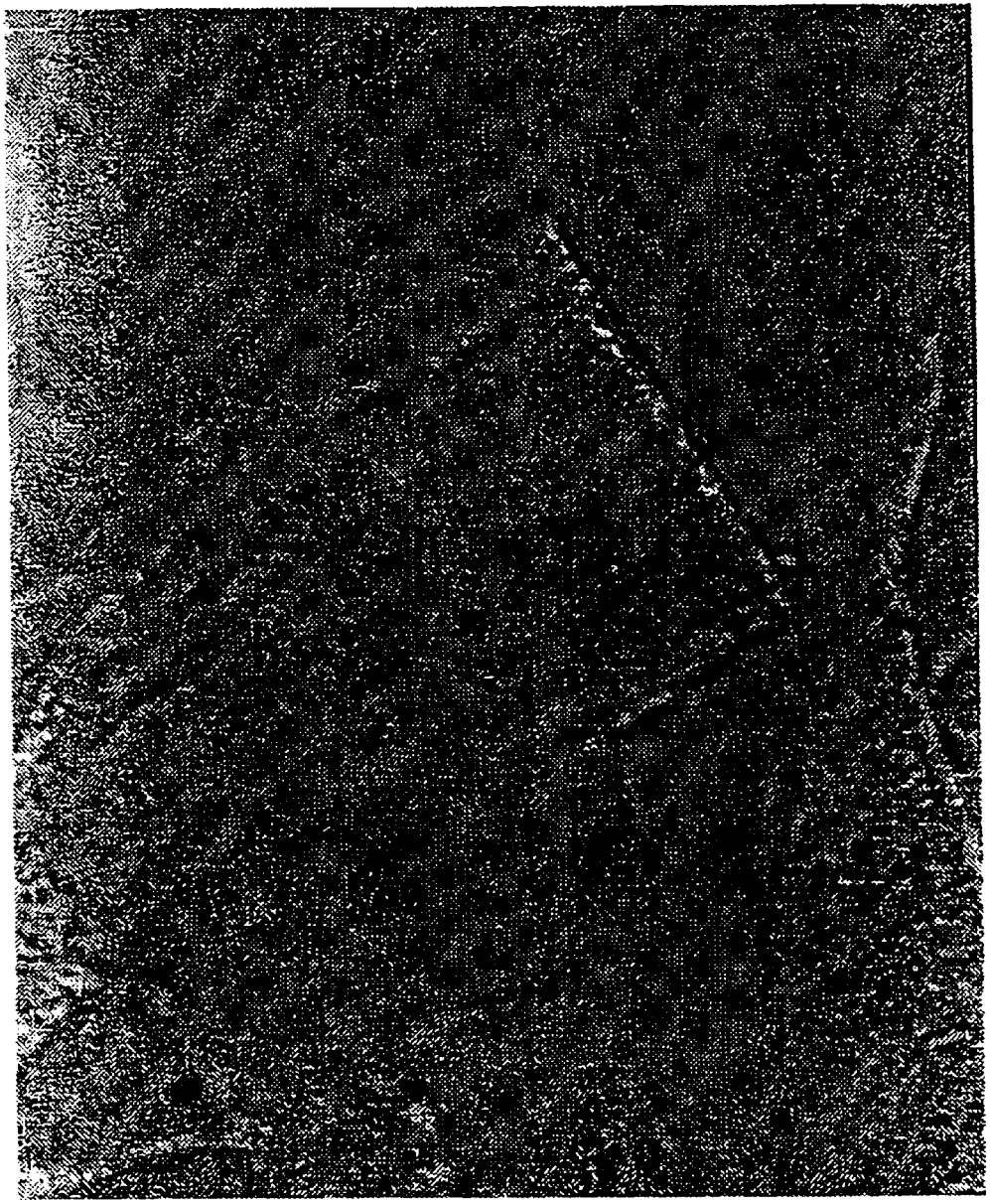
FIG. 2 represents a microscope test of a cross section of an implant according to the prior art.

The same microscopic examination was carried out on an implant produced using a known technique obtained in accordance with U.S. Pat. No. 5,366,734 which under 1100× enlargement reveals a homogeneous distribution of the two components as in FIG. 2.

Kinetics of in Vitro Release

The implants prepared in accordance with Example 1 were tested in vitro in order to examine the kinetics of releasing avoreline.

The test was carried out under the following conditions.

Five implants were introduced into one flask and the 5 ml of phosphate buffer at pH 7.4 were added. The test was conducted at 37° C. for a period of 210 days, continuously stirring the solution using 100 turns per minute.

Each week the buffer solution containing the active constituent released over the same period was sampled and analysed, while 5 ml of phosphate buffer were added to the flask as above.

The content of avoreline in the solutions was determined by means of HPLC under the following conditions:

| | |
|---|---|
| Column: | Vydac 218TP 54300A medium, 5 µm, dimensions 250 x 4.6 mm |
| Mobile phase: | 750 ml phosphoric acid 0.1M were added to 250 ml of acetonitrile and the pH was corrected to 2.5 with triethylamine and the mixture filtered over an FH type filter (millipore). |
| Output: | 1.5 ml/minute. |
| Temperature: | 30° C. |
| Determination: | UV at 220 nm |
| Injection: | volume 10 µl |
| Analysis time: | 15 minutes |

Figure 3:
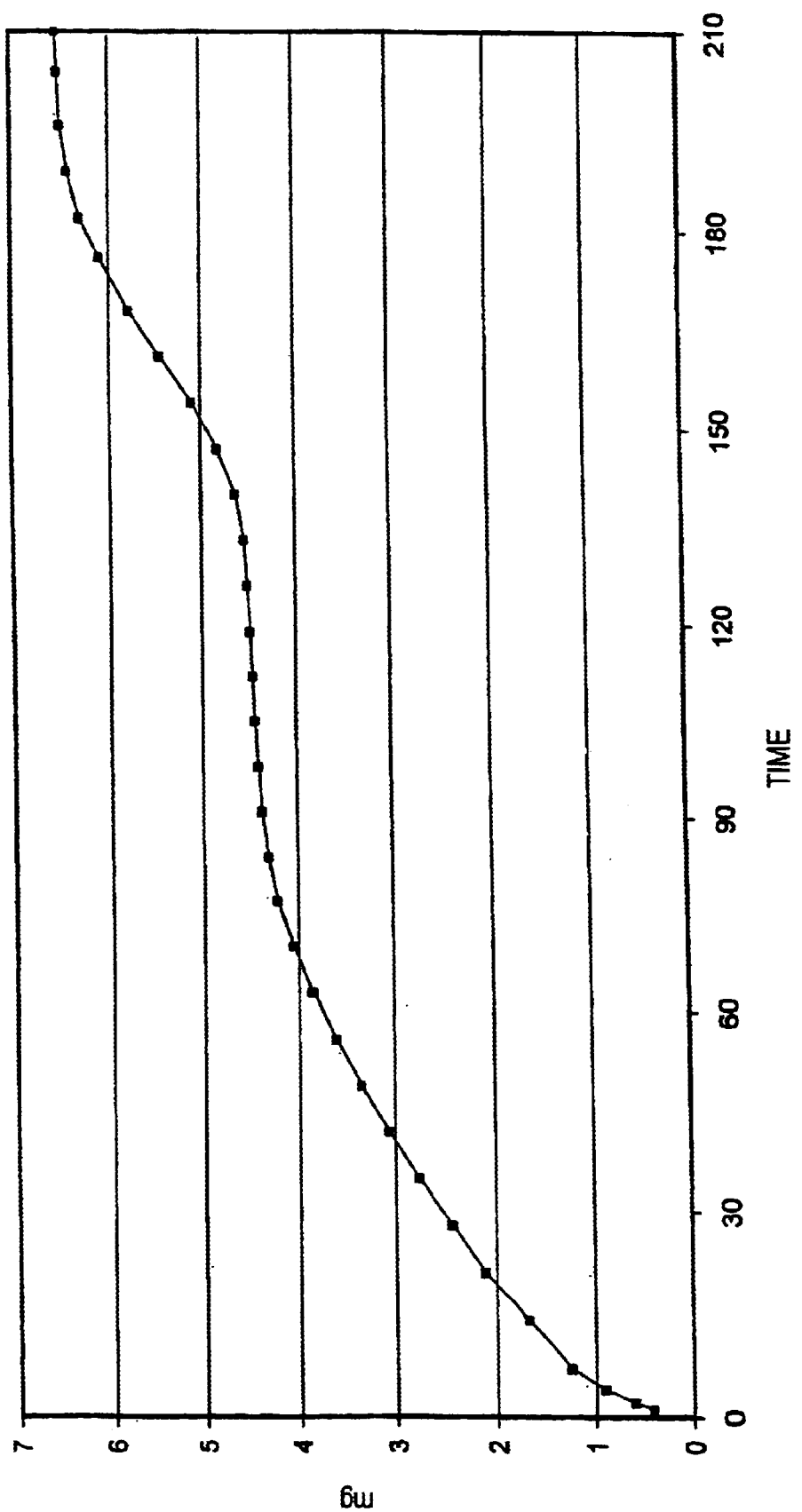
FIG. 3 represents the cumulative amount of avoreline released from implants of Example 1.

The results are shown in FIG. 3 in which in the X-axis shows the time expressed in days and the Y-axis shows the cumulative quantity of avoreline released expressed in mg.

EXAMPLE 2

Example 1 was repeated, with the difference that implants were produced with a diameter of 1.5 mm, length 15 mm and avoreline content of 20.9% by weight.

Figure 4:
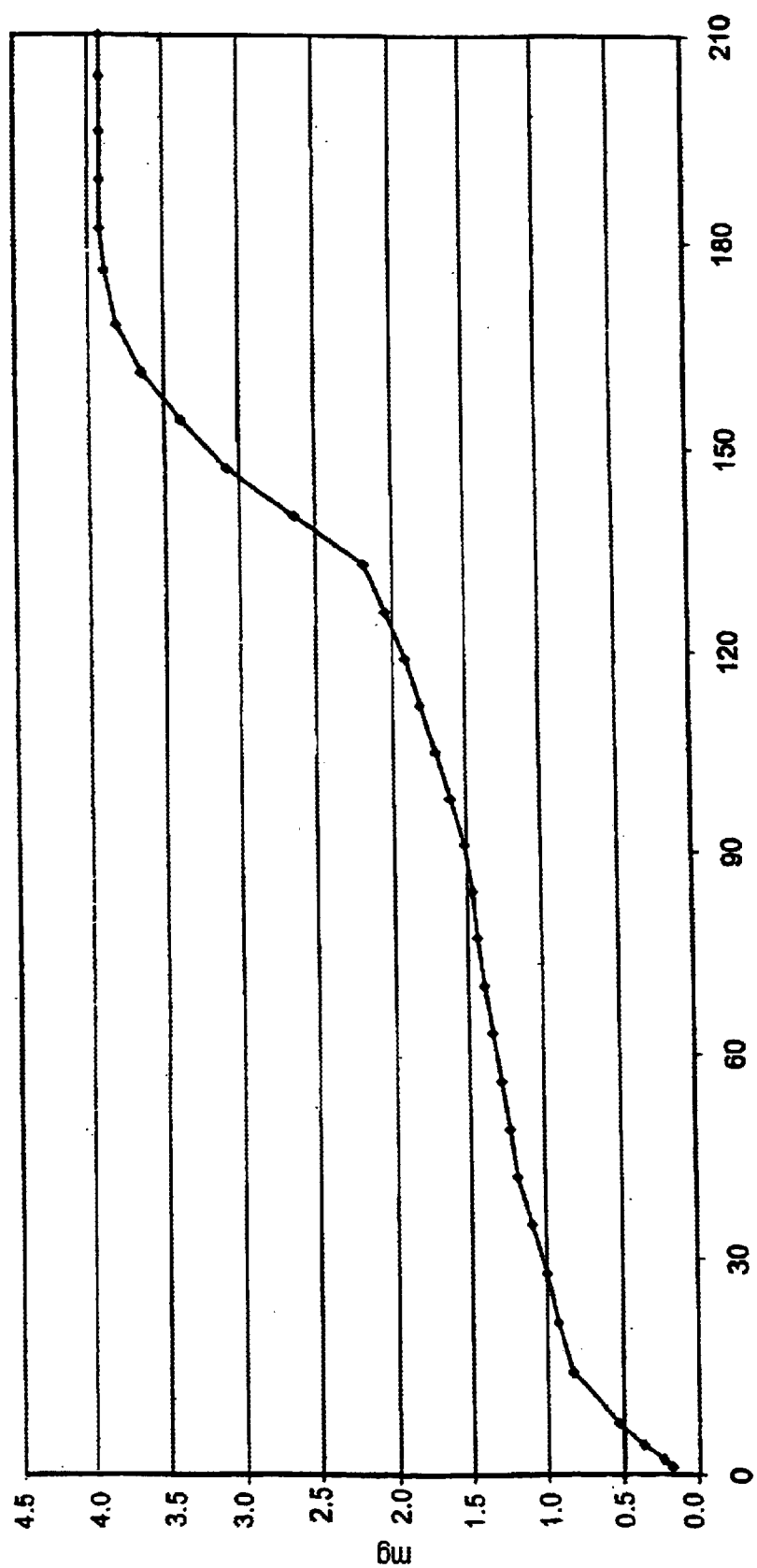
FIG. 4 represents the cumulative amount of avoreline released from implants of Example 2.

Microscopic examination produced similar results to Example 1. The results of the in vitro release test are shown in FIG. 4 in which the parameters are the same as those in FIG. 3.

EXAMPLE 3

Example 1 was repeated with the difference that PLGA having a molecular weight of 121,900 D was used and implants were prepared having a diameter of 1.5 mm, length 18 mm and avoreline content of 27.9% by weight.

Microscopic examination and the release test produced similar results to Example 1.

EXAMPLE 4

9 grams of avoreline were mixed thoroughly with 24 g of polylactic-glycolic acid (PLGA).

The avoreline had the following characteristics:
acid-alkalimetric titer: 90.1 % by weight;
pKa : 6.15 –9.70–12.02:
granulometric distribution: between 1 and 60 micrometres.

The PLGA had the following characteristics:
molecular weight: 121,900 D;
molar ratio between lactic monomer and glycolic monomer: 70:30;
granulometric distribution: in 90% of cases between 50 and 150 micrometres.

The mixture obtained was granulated wet by adding 6 ml of water using a 1.6 mm grid.

The granulate obtained was desiccated for 12 hours at a temperature of 25 ° C. in a current of dry air.

After drying the water content in the granulate was 1.8% by weight.

Extrusion and the subsequent operations were conducted as in Example 1.

The implants obtained had an avoreline titer of 27.6% by weight.

Microscopic examination and the release test produced similar results to Example 1.

EXAMPLE 5

6 grams of tryptoreline were thoroughly mixed with 14 grams of PLGA.

The tryptoreline had a titer of 90.5% by weight and a granulometric distribution of between 1 and 60 micrometres.

The PLGA had a molecular weight of 121,900 D, a molar ratio between lactic monomer and glycolic monomer of 70:30 and a 90% granulometric distribution of between 50 and 150 micrometres.

The mixture obtained was granulated wet by adding 8 ml of ethanol using a 1.6 mm grid.

The granulate obtained was desiccated for 12 hours at a temperature of 25° C. in a current of dry air.

After desiccation the ethanol content in the granulate was 1.0% by weight.

Extrusion and the subsequent operations were conducted as in Example 1.

The implants obtained had an avoreline titer of 24.7% by weight. Microscopic examination and the release test produced similar results to Example 1.

EXAMPLE 6

6 grams of gosereline were thoroughly mixed with 14 grams of PLGA.

The gosereline had a titer of 89.5% by weight and a granulometric distribution of between 1 and 60 micrometres.

The PLGA had a molecular weight of 121,900 D, a molar ratio between lactic monomer and glycolic monomer of 70:30 and a 90% granulometric distribution between 50 and 150 micrometres.

The mixture obtained was granulated wet by adding 8 ml of ethanol using a 1.6 mm grid.

The granulate was desiccated for 12 hours at a temperature of 25° C. in a current of dry air.

After desiccation the ethanol content in the granulate was 1.1% by weight.

Extrusion and the subsequent operations was-carried-out as in Example 1.

The implants obtained had a gosereline titer of 24.9% by weight.

Microscopic examination and the release test produced similar results to Example 1.

Clinical experimentation

Clinical trials were conducted in 60 patients suffering from prostate tumours, using subcutaneous implants prepared in accordance with this invention.

A group of patients was treated with implants having an avoreline content of 10 mg and a second group was treated with implants having an avoreline content of 15 mg.

The results of the experiments are shown in FIGS. 5 to 8.

The graphs for these Figures can be interpreted as follows:

Graph a) represents the average plasma concentration of the FSH;

Graph b) represents the average plasma concentration of testosterone;

Graph c) represents the average plasma concentration of LH;

Graph d) represents the average plasma concentration of avoreline;

line e) is the line of castration with reference to testosterone.

Figure 5:
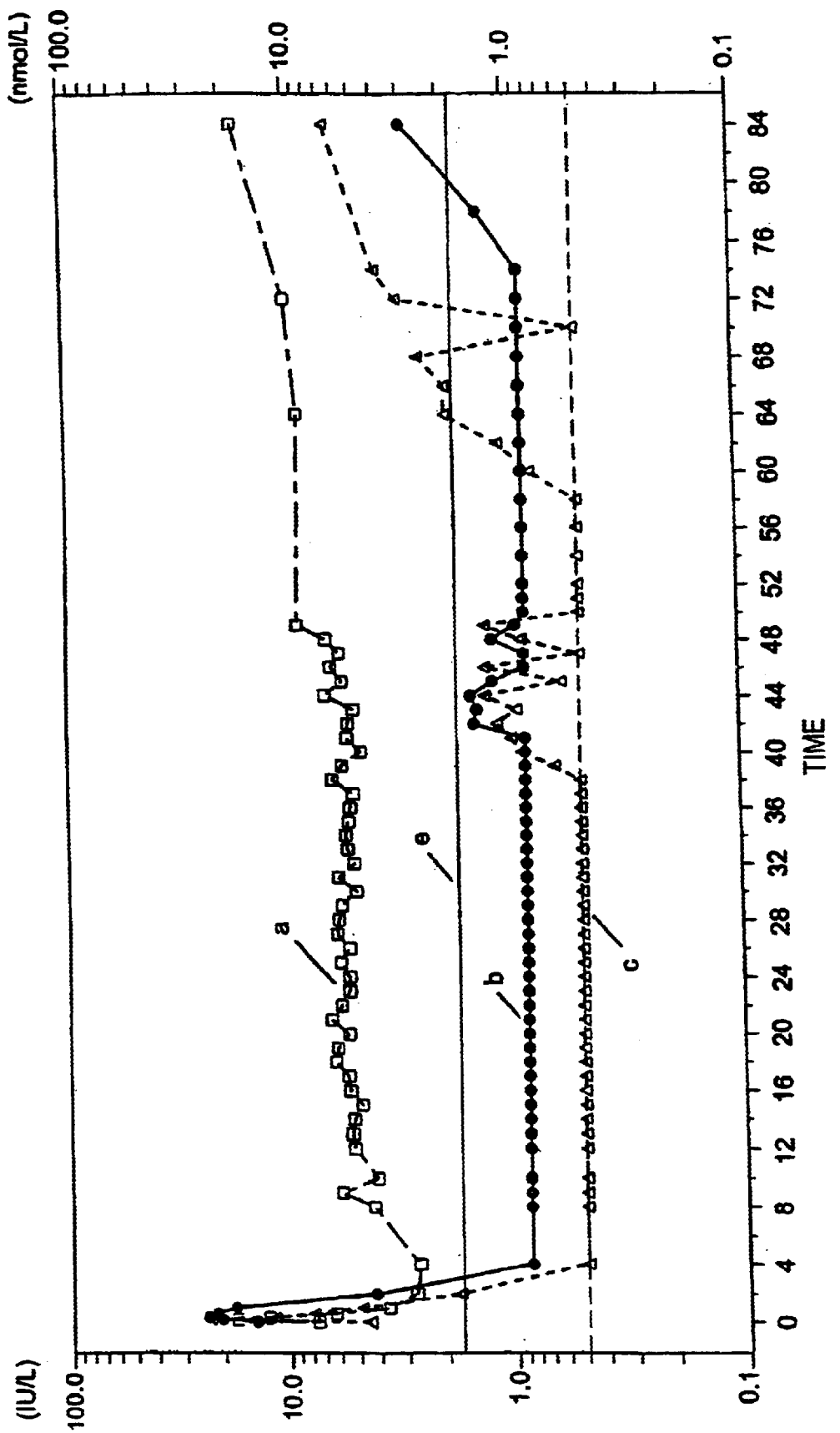
FIG. 5 represents the plasmatic concentration of LH, FSH and testosterone by clinical experimentation using implants having an avoreline content of 10 mg.
Figure 6:
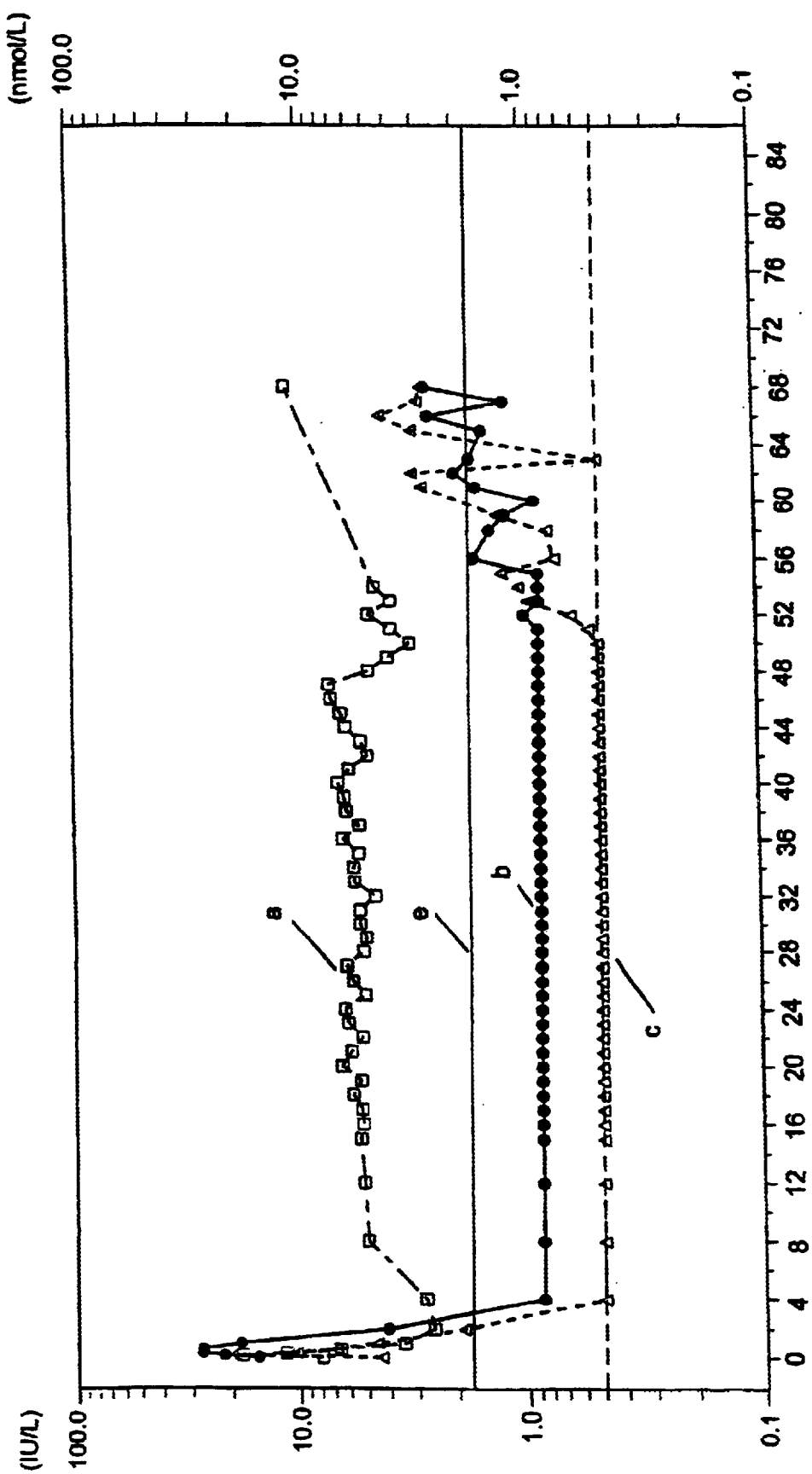
FIG. 6 represents the plasmatic concentration of LH, FSH and testosterone by clinical experimentation using implants having an avoreline content of 15 mg.
Figure 7:
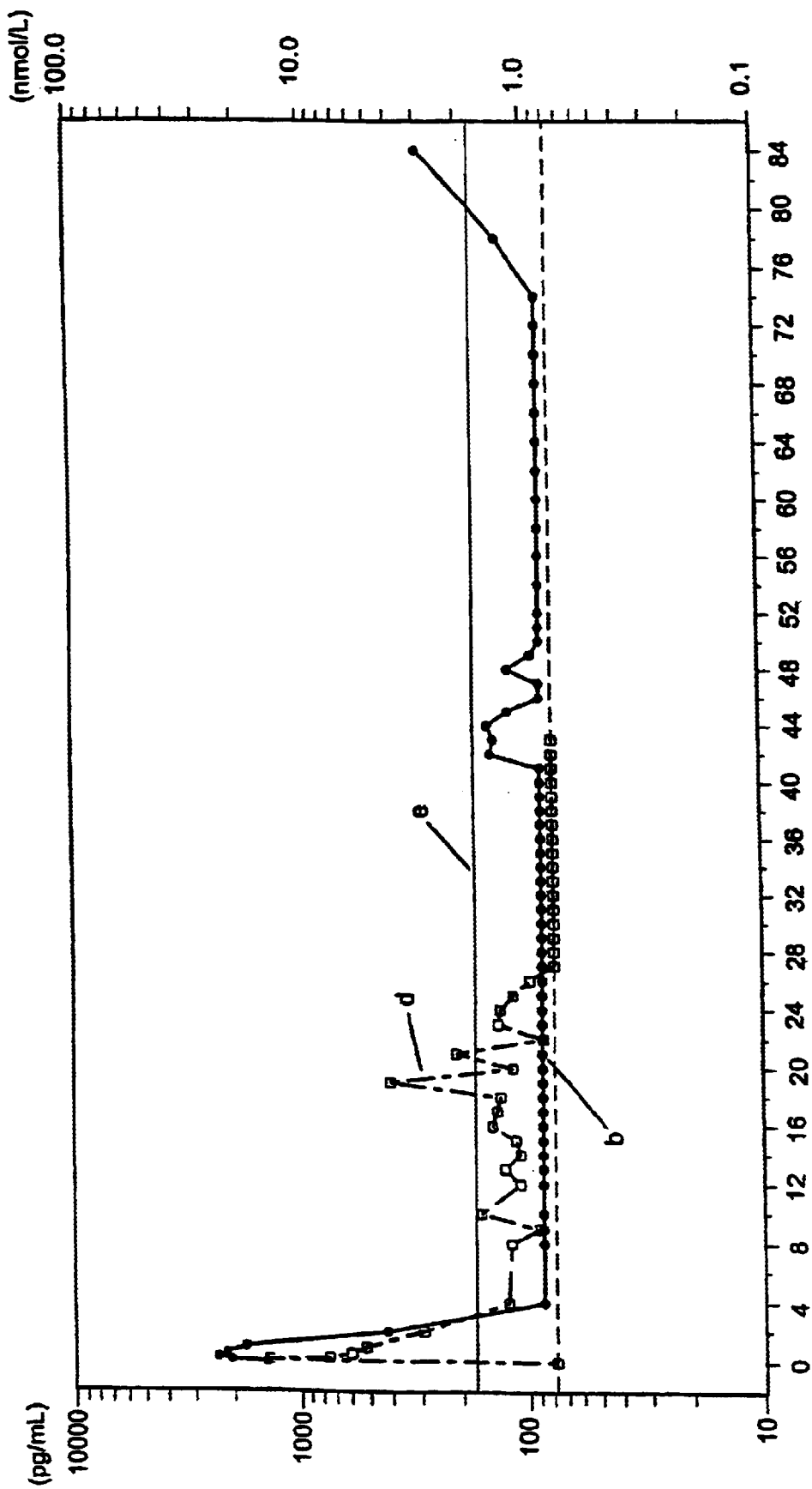
FIG. 7 represents the plasmatic concentration of avoreline and testosterone by clinical experimentation using implants having an avoreline content of 10 mg.
Figure 8:
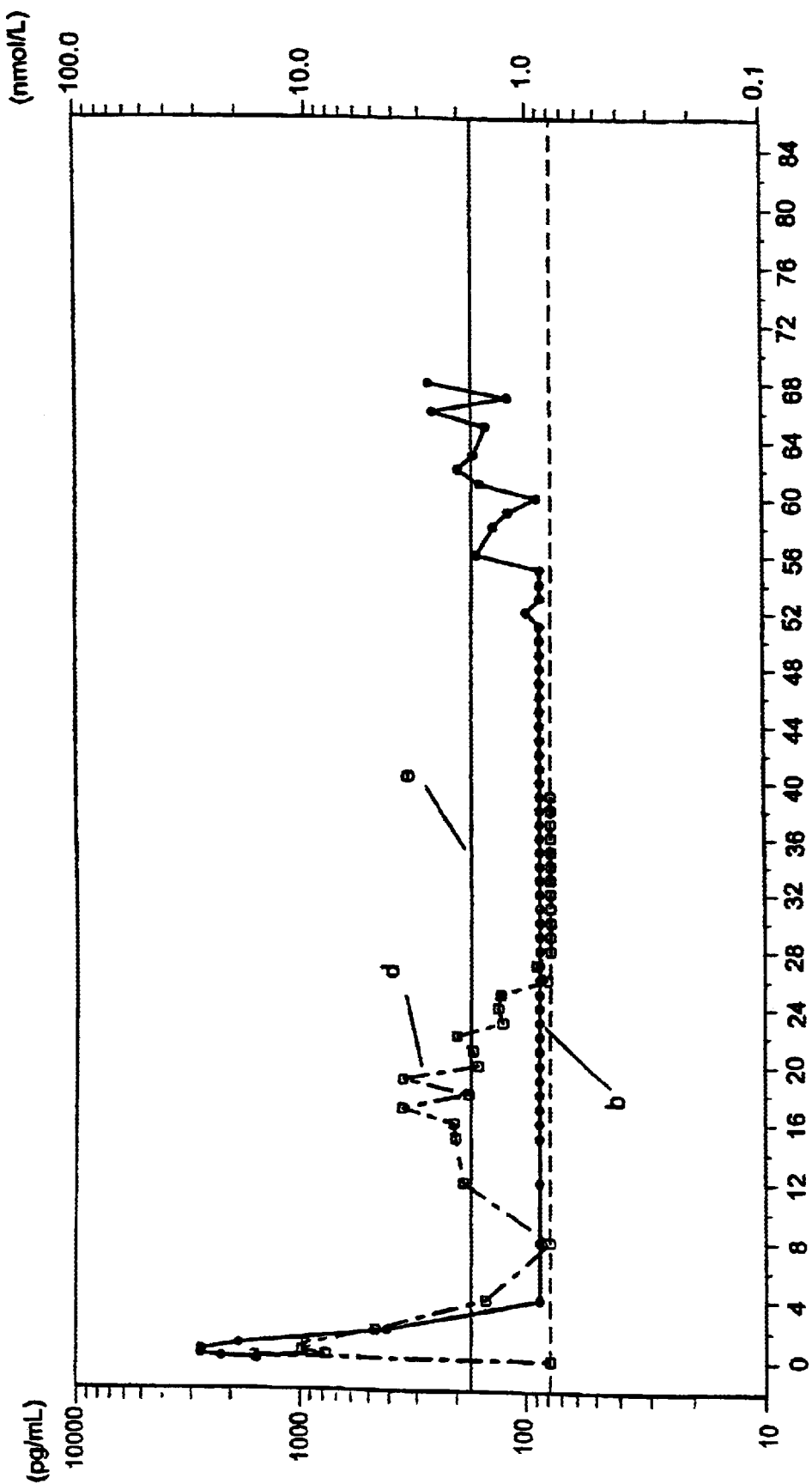
FIG. 8 represents the plasmatic concentration of avoreline and testosterone by clinical experimentation using implants having an avoreline content of 15 mg.

FIG. 5 and FIG. 7 refer to the use of implants having an avoreline content of 10 mg while FIGS. 6 and 8 refer to the use of implants having an avoreline content of 15 mg.

With reference to FIGS. 5 and 6, the left ordinate shows the plasma concentration of LH and FSH expressed in IU/L and the right ordinate shows the plasma concentration of testosterone expressed in nmol/L.

With reference to FIGS. 7 and 8, the left ordinate shows the plasma concentration of avoreline expressed in pg/mL and the right ordinate shows the plasma concentration of testosterone expressed in nmol/L.

In all the Figures, the time from implant insertion, expressed in weeks, is shown on the X-axis.

As can be seen from these Figures, using the implants in accordance with this invention, testosterone is suppressed within four weeks after the implant is inserted with this effect lasting for a period of between approximately seven months and approximately twelve months.

The plasma concentrations which can be determined for avoreline were measured for approximately 6 months after inserting the implant.

What is claimed is:

1. A composition suitable for the preparation of subcutaneous implants having a release time of at least six (6) months comprising a polylactic-glycolic acid copolymer (PLGA) and a peptide, said peptide being dispersed in the PLGA matrix in the form of particles having heterogeneous dimensions with diameters ranging from 1 to 60 micrometers.

2. The composition as claimed in claim 1, wherein when the peptide is brought into contact with an aqueous physiological solution it is released in three stages, with the first stage of release involving diffusion, the second stage of release involving swelling of the PLGA and the third stage of release involving PLGA degradation.

3. The composition as claimed in claim 1, wherein said PLGA has a molecular weight between 50,000 and 150,000 and a molar ratio of lactic monomer to glycolic monomer between 50:50 and 95:5.

4. The composition as claimed in claim 3, wherein said PLGA has a molecular weight of between 100,000 and 150,000 and a molar ratio of lactic monomer to glycolic monomer between 70/30 and 75/25.

5. The composition as claimed in claim 1, wherein said peptide is selected from the group consisting of avoreline, tryptoreline, leuproreline and gosereline.

6. The composition as claimed in claim 1, wherein said peptide is avoreline.

7. The composition as claimed in claim 1, wherein said peptide is tryptoreline.

8. The composition as claimed in claim 1, wherein said peptide is gosereline.

9. The composition as claimed in claim 1, wherein the peptide content is between 20 and 40%.

10. Process for preparing compositions suitable for preparing subcutaneous implants as claimed in claim 1, comprising the steps of:

a) homogeneously mixing a peptide in particle form whose diameters range from 1 to 60 micrometers, when dry, with PLGA;

b) granulating the mixture obtained from step a) by adding a liquid;

c) drying the granulate of step b) until the residual liquid content ranges from 0.5 to 2.0%, by weight; and d) extruding the mixture obtained from step c).

11. The process as claimed in claim 10, wherein the residence time in the extruder of step d) is from 4 to 6 minutes at a temperature which ranges from 30° C. on entering the extruder to no higher than 110° C. on leaving the extruder.

12. The process as claimed in claim 10, wherein the quantity of peptide used in step a) is between 20 and 40%, by weight.

13. The process according to claim 12, wherein the quantity of peptide is between 20 and 36%, by weight.

14. The process as claimed in claim 10, wherein when said granulating liquid is ethanol or water, the quantity of liquid added is between 10 and 60 parts per 100 parts, by weight, of the mixture.

15. Process as claimed in claim 14, wherein said ethanol or water is between 20 and 45 parts per 100 parts of mixture, by weight.

16. Process as claimed in claim 10, wherein the extrudates obtained by extrusion from step d) have a diameter of between 1.0 and 1.7 mm, and a length of between 10 and 30 mm.

17. Process as claimed in claim 10, wherein said extrudates have a diameter of between 1.3 and 1.5 mm, and a length of between 15 and 24 mm.

18. Subcutaneous implants obtained from the composition as claimed in claim 1.

19. Subcutaneous implants prepared according to the process of claim 10.

20. Subcutaneous implants as claimed in claim 18, having a diameter of between 1.3 and 1.5 mm, a length of between 15 and 24 mm and a peptide content of between 5 and 20 mg.

21. Subcutaneous implants according to claim 18, wherein said peptide is selected from the group consisting of avoreline, tryptoreline, leuproreline and gosereline.

22. The composition as claimed in claim 1, wherein the peptide content is between 20% and 36%, by weight.

* * * * *